(12) United States Patent
Perrino

(10) Patent No.: US 6,595,968 B1
(45) Date of Patent: Jul. 22, 2003

(54) HAND-HELD DOUCHE APPARATUS

(76) Inventor: Joseph M. Perrino, 1210 Morts Pass, Wyoming, OH (US) 45215

( * ) Notice: Subject to any disclaimer, the term of this patent is extended or adjusted under 35 U.S.C. 154(b) by 291 days.

(21) Appl. No.: 09/589,698

(22) Filed: Jun. 8, 2000

Related U.S. Application Data

(63) Continuation-in-part of application No. 09/378,158, filed on Aug. 16, 1999.

(51) Int. Cl.$^7$ ............................................. A61M 31/00
(52) U.S. Cl. ...................................................... 604/279
(58) Field of Search ........................... 604/6.12, 30, 32, 604/35, 37, 39, 173, 181, 187, 191, 212, 279, 295

(56) References Cited

U.S. PATENT DOCUMENTS

| | | | |
|---|---|---|---|
| 3,254,647 A | | 6/1966 | Vogel |
| 4,601,709 A | * | 7/1986 | Kabbaby ..................... 604/150 |
| 4,650,470 A | | 3/1987 | Epstein |
| 5,071,104 A | | 12/1991 | Witt et al. |
| 5,167,646 A | | 12/1992 | Swafford |
| 5,304,116 A | * | 4/1994 | Cornelius ..................... 604/39 |
| 5,987,659 A | | 11/1999 | Cannizzaro |
| 5,991,937 A | | 11/1999 | Safara |
| 6,206,862 B1 | * | 3/2001 | Giamanco et al. .......... 604/279 |

* cited by examiner

*Primary Examiner*—Michael J. Hayes
*Assistant Examiner*—Kevin C. Sirmons
(74) *Attorney, Agent, or Firm*—Mark F. Smith; Smith, Brandenburg Ltd.

(57) ABSTRACT

The present invention is directed to a hand held douche apparatus which can be used to direct a flow of water or a flow of water containing a medicated or cleansing solution for providing medication or for personal hygiene. In a preferred embodiment of the invention, the hand held douche apparatus comprises a mixing assembly, a diverter assembly for attaching to a suitable pressurized water source, and a spray assembly. The mixing assembly comprises a container for providing a reservoir for storing a medication solution or a liquid cleansing agent and a cap for attaching to the container and includes a first fluid passage having an inlet port for receiving a stream of pressurized water and an outlet port for directing the stream of pressurized water to the spray assembly and a second fluid passage for providing flow communication with the first fluid passage and the reservoir for inducing the medication solution or the liquid cleansing agent into the water stream. Disposed within the second fluid passage is a back-flow prevention valve for preventing water flow from the first fluid passage into the reservoir.

17 Claims, 5 Drawing Sheets

HAND-HELD DOUCHE APPARATUS

RELATED APPLICATION

This is a continuation-in-part of U.S. patent application Ser. No. 09/378,158, filed: Aug. 16, 1999.

BACKGROUND OF THE INVENTION

The present invention is directed to a douche apparatus which can be used for personal hygiene and more specifically, to a new and novel hand-held douche apparatus which can direct a flow of water or a flow of water containing a medicated or cleansing solution for providing medication or for personal hygiene.

Various devices for directing a water stream for cleansing the anal-genital area of a human have been developed and have been found to provide superior cleansing than that provided by conventional means. Apparatus have also been developed that operate to introduce medicated solutions or cleansing agents into the water stream. Water streams containing such medicated or cleansing solutions have been found to be useful in providing relief for those who suffer from certain medical ailments or require particular hygienic conditions. Such devices for directing water streams for hygienic cleansing are often free standing fixtures with attached plumbing that provides water and drainage and often have reservoirs for storing medicated solutions or cleansing agents which mix with the water stream during operation. Unfortunately, however, these devices are relatively expensive and require a significant amount of extra space. Other devices have been developed that are adapted for attaching to conventional toilets. Such devices, however, typically require a nozzle located inside the toilet bowl, thus modifying the appearance of the toilet as well as making them more difficult to clean, which can result in mildew and mold, often causing unpleasant odors. In addition, these devices often do not direct the water stream to the desired body area, thereby, reducing their effectiveness.

Devices, such as various hand-held douche apparatus, have been developed for directing a water stream for cleansing or for providing medication to the anal-genital area of the user. These devices often utilize a container for storing a liquid medication or cleansing solution. The solution is typically induced into the water stream using the pressure differential created by directing the fluid stream over a passage leading into the solution storage container. Until now, such devices, however, ordinarily would not provide means for controlling the amount of solution being drawn into the water stream and can therefore result in to much or to little of the solution being mixed with the water stream. Further, until now, in order to prevent pressure build-up in the storage container that can result in water spirts, devices utilizing a pressure differential to draw the solution out of the storage container require the water stream shut off valve to be located upstream of the storage container. Unfortunately, positioning the water stream shut off valve upstream of the storage container has the disadvantage of being awkward and generally more difficult for the user to control the fluid stream.

Accordingly, a need exist for a new and novel hand-held douche apparatus which can be used for personal hygiene; that includes means for mixing an additive, such as a liquid medication or cleansing agent into the water stream; that permits the user to easily control the amount of additive being induced into the water stream; that permits a water stream having a constant and consistent concentration of medication or cleansing agent; and provides means for controlling the pressure of the discharging water stream. The hand-held douche apparatus should also be relatively inexpensive to manufacture and maintain; relatively durable, lightweight and simple in construction; easy to operate; and easy to install to conventional plumbing systems.

SUMMARY OF THE INVENTION

The present invention is directed to a hand held douche apparatus which can be used for applying medication or for personal hygiene. In a preferred embodiment of the invention, the hand held douche apparatus comprises a mixing assembly, a diverter assembly for attaching to a suitable pressurized water source, and a spray assembly for dispensing a fluid stream. The mixing assembly comprises a container for providing a fluid reservoir for storing an additive, such as a medication solution or a liquid cleansing agent, and a cap for attaching to the container and having an inlet port for receiving a stream of pressurized water and an outlet port for. directing the stream of pressurized water to the spray assembly. The inlet port and the outlet port are interconnected by a first flow passage comprising a constricted area. The cap further comprises a second fluid passage for providing flow communication with the first fluid passage and the fluid reservoir for inducing the additive into the water stream, and a vent in flow communication between the fluid reservoir and the outside atmosphere. Disposed within the second fluid passage is a back-flow prevention valve for preventing water flow from the first fluid passage into the fluid reservoir.

In another preferred embodiment of the invention, the constricted area cooperates with the water stream to create a pressure differential to cause the additive to flow upwardly out of the fluid reservoir through the second fluid passage to mix with the water stream.

In another preferred embodiment of the invention, the hand-held douche apparatus includes means for regulating the amount of additive being induced into the water stream.

In another preferred embodiment of the invention, the hand-held douche apparatus includes means for inducing a constant flow of an additive into the water stream.

In another preferred embodiment of the invention, disposed within the, second fluid passage is a fluid control valve which operates to close off the second flow passage entirely or to open the second flow passage to varying degrees to control the flow through the second flow passage.

In another preferred embodiment of the invention, the hand-held douche apparatus comprises means for installing to a conventional plumbing system.

In another preferred embodiment of the invention, the hand-held douche apparatus comprises means for installing to a conventional plumbing system having hot and cold water sources for regulating the temperature of the pressurized water stream.

In another preferred embodiment of the invention, the hand-held douche apparatus comprises means for regulating the amount of water being dispensed.

In another preferred embodiment of the invention, the hand-held douche apparatus is adapted for receiving a variety of nozzle configurations.

A primary object of the present invention therefore, is to provide a hand-held douche apparatus which can be used for personal hygiene.

Another primary object of the present invention is to provide a hand-held douche apparatus having means for easily mixing an additive, such as a liquid medication or cleansing agent, into the water stream.

Another primary object of the present invention is to provide a hand-held douche apparatus that permits the user to control the amount of additive entering into the water stream.

Another primary object of the present invention is to provide a hand-held douche apparatus that permits a water stream having a consistent and steady concentration of additive, such as a liquid medication or cleansing agent.

Another primary object of the present invention is to provide a hand-held douche apparatus that provides means for controlling the pressure of the discharging water stream.

Another primary object of the present invention is to provide a hand-held douche apparatus that can be used with conventional plumbing systems.

Another primary object of the present invention is to provide a hand-held douche apparatus that provides means for controlling the temperature of the water stream.

Another primary object of the present invention is to provide a hand-held douche apparatus that is relatively inexpensive to manufacture and maintain.

Another primary object of the present invention is to provide a hand-held douche apparatus that is simple in construction.

Another primary object of the present invention is to provide a hand-held douche apparatus that is easy to operate.

Another primary object of the present invention is to provide a hand-held douche apparatus that is easy to install to conventional plumbing systems.

Another primary object of the present invention is to provide a hand-held douche apparatus that is relatively durable and lightweight in construction.

These and other objects and advantages of the invention will be apparent from the following description, the accompanying drawings and the appended claims.

DETAILED DESCRIPTION OF THE PREFERRED EMBODIMENTS

Figure 1:
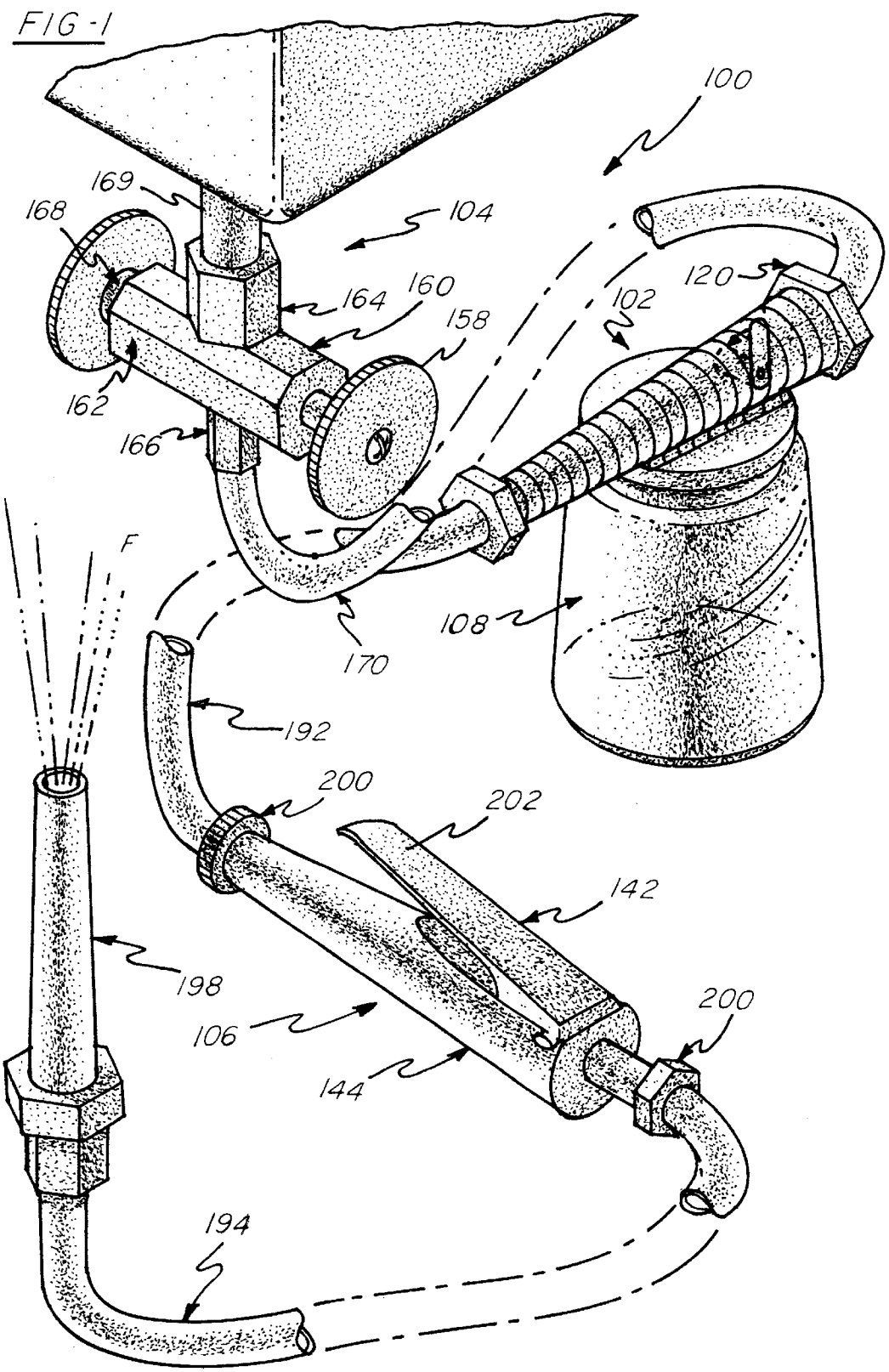
FIG. 1 is a perspective view of the hand held douche apparatus of the present invention showing the mixing assembly having a container for providing a fluid reservoir, the diverter assembly for attaching to a suitable pressurized water source, and a spray assembly.

Referring to FIG. 1, the hand-held douche apparatus 100 of the present invention is shown comprising a mixing assembly 102, a diverter assembly 104 for attaching to a suitable pressurized water source, and a spray assembly 106.

Figure 2:
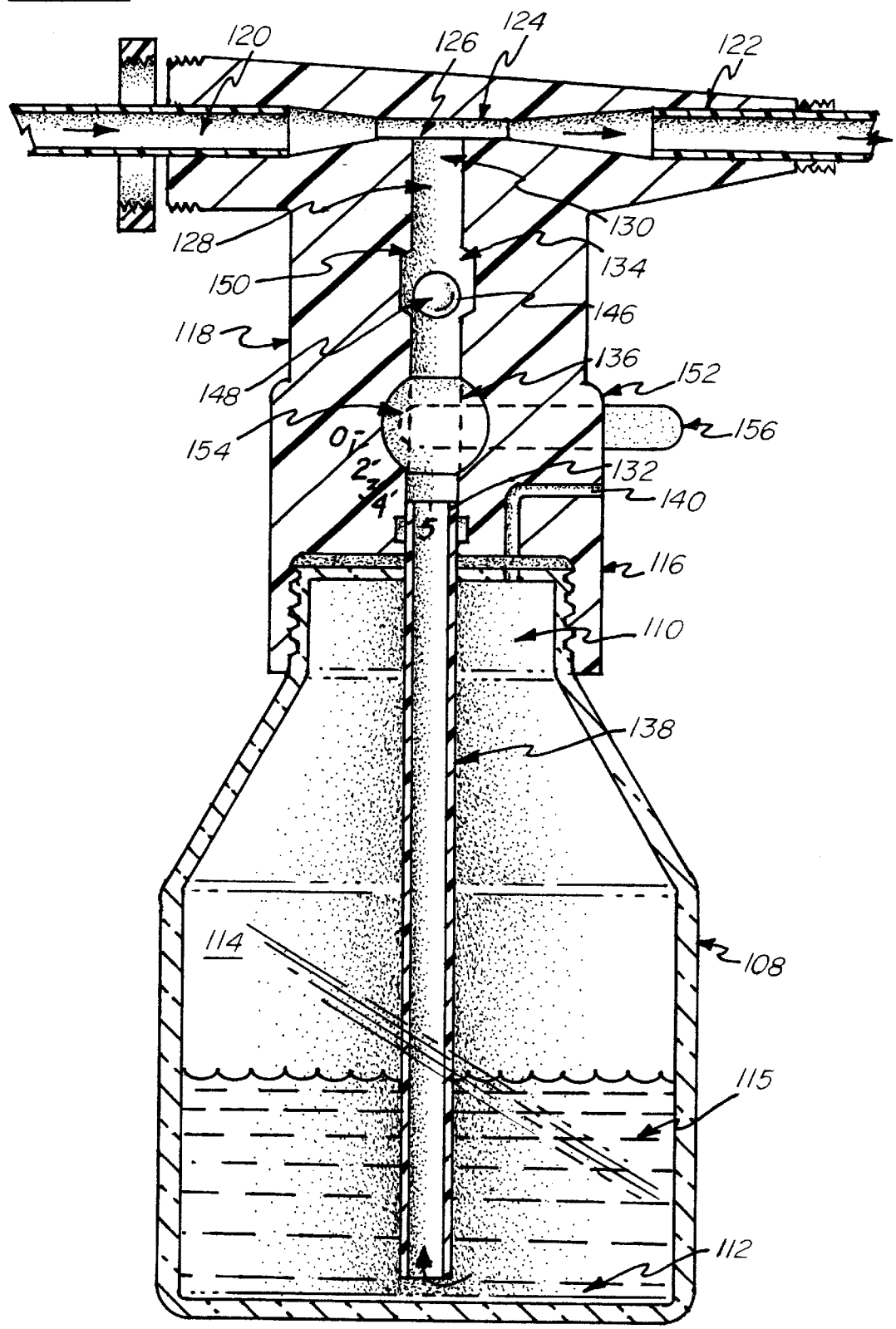
FIG. 2 is a sectional view of the mixing assembly of the present invention.

Referring to FIGS. 1 and 2, the mixing assembly 102 includes a container 108 having an open upper end 110 and an opposed closed lower end 112 providing a fluid reservoir 114 there between for storing an additive 115 such as a medication solution or a liquid cleansing agent. The open upper end 110 is externally threaded for mating with a corresponding internally threaded annular collar 116 of a cap 118, The cap 118 and the container 108 are preferably made of a relatively rigid plastic, however it should be understood that other materials, such as brass, aluminum and other metals may be used.

As shown in FIGS. 1 and 2, the cap 118 further includes an inlet port 120 and an outlet port 122. The inlet port 120 and the outlet port 122 are interconnected by a first flow passage 124 comprising a constricted area 126 having a diameter smaller than the diameters of either the inlet port 120 and the outlet port 122. A second flow passage 128 is provided having a first end 130 and a second end 132, and a first cylindrical section 134 and a second cylindrical section 136 there between. The second flow passage 128 extends from the transverse wall of the constricted area 126 of the first flow passage 124 downwardly towards the annular collar 116 and connects with one end of a suction tube 138. The suction tube 138 is connected to the second end 132 of the second flow passage 128 by any suitable means, such as by friction fitting or glueing, and extends downwardly into the fluid reservoir 114 adjacent to the closed lower end 112 of the container 108. Preferably, the suction tube 138 is formed from a flexible elastomeric material, however it should now be apparent to those skilled in the art that the suction tube 138 may be formed from a relatively rigid material, such as a rigid plastic or a metal. The cap 118 further includes a vent 140 that provides flow communication between the fluid reservoir 114 and the outside atmosphere A thereby allowing air to enter the fluid reservoir 114 during operation of the hand-held douche apparatus 100. It should now be apparent to those skilled in the art that such venting of the fluid reservoir 114 during operation prevents pressure build up in the reservoir 114 thereby eliminating the occurrence of water spirts and permits the water stream activation valve 142 for turning on or shutting off the flow of fluid being discharged to be located downstream of the storage container 108, such as in the handle 144 of the spring assembly 102 hereinafter described. Thus, the hand-held douche apparatus 100 of the present invention has the advantage of being relatively easy for the user to operate and to control the discharging fluid stream.

As shown, the first cylindrical section 134 has a larger diameter than the first end 130 or the second end 132 of the second flow passage 128 and is provided with a conventional backflow prevention valve 146 having a valve ball 148 disposed within the first cylindrical section 134. The diameter of the first cylindrical section 134 is sufficiently larger than the diameter of the valve ball 148 to permit fluid to flow upwardly around the valve ball 148. In contrast, the lower upstream end of the first cylindrical section 134 is tapered to provide a ball seat 150 for receiving the valve ball 148 to effectively block flow from flowing down through the second flow passage 128 and into the fluid reservoir 114.

The second flow passage 128 further includes a conventional fluid control valve 152 which operates to close off the second flow passage 128 entirely or to open the second flow passage 128 to varying degrees to control the amount of the fluid additive 115 flowing through the second flow passage 128. As shown in FIG. 2, the fluid control valve 152 is a conventional rotary valve having a rotary member 154 positioned within a second cylindrical section 136. The rotary member 154 is coupled to an external handle 156 such that when the handle 156 is in a first direction, as shown in FIG. 2, the rotary member 154 permits a substantially unrestricted flow of the fluid additive upwardly through the second fluid passage 128. As the handle 156 is rotated, the rotary member 154 increasingly restricts the amount of additive 115 that can flow upwardly through the second flow passage 128 until the rotary member 154 substantially blocks any of the additive 115 from flowing upwardly through the second flow passage 128. It should now be apparent to those skilled in the art that the combination of the fluid control valve 152, back flow prevention valve 146, and the vent 140 cooperate to permit the user to easily detach the container 108 from the cap 118 to add additive 115, such as a liquid medication or cleansing agent, into the fluid reservoir 114 without requiring the user to disconnect the hand-held douche assembly 100 from the source of pressurized water or from preventing water from entering the diverter assembly 104 such as by use of the shut-off valve 158 of the diverter assembly 104 (as described herein below). In addition, the back flow prevention valve 146 and the vent 140 prevent water from entering the fluid reservoir 114 and continuously dilute the additive 115 and cooperate to allow the user to accurately control the amount of additive 115 being induced into the water stream. In this way, the hand-held douche apparatus 100 of the present invention provides the user with a stream having a constant and consistent concentration of additive.

Referring to FIG. 1, in a preferred embodiment of the invention, the diverter assembly 104 comprises a conventional three-branch plumbing connector 160 having one inlet 162 and two outlet branches, 164 and 166, respectively. A flow shut-off valve 158 is provided for blocking the flow of water through the diverter assembly 104. The inlet 162 is connected to an existing water supply, such as the water supply line 168 used for filling a conventional toilet reservoir (not shown). The first outlet branch 164 is adapted for receiving one end of an existing toilet water supply line 169 and the second outlet branch 166 is adapted for receiving one end of flexible tubing 170. As shown in FIGS. 1 and 2, the other end of the flexible tubing 170 is adapted for mating with the inlet port 120 of the cap 118 by means of a conventional coupling or by means of a press-fit, glueing, or other suitable means.

Figure 3:
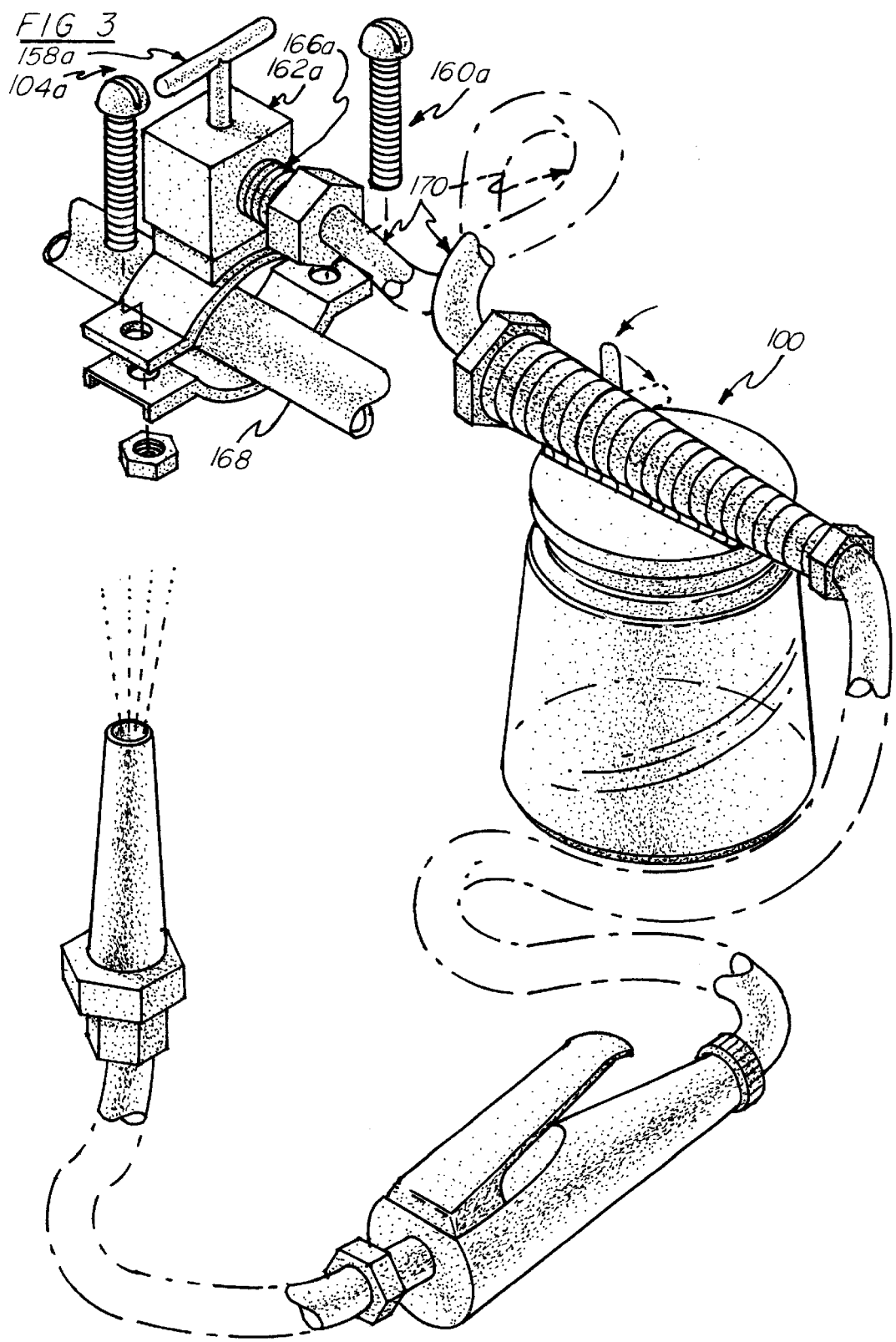
FIG. 3 is a perspective view of another preferred embodiment of the present invention showing an alternate diverter assembly comprising a two-branch plumbing connector.

Another preferred embodiment of the hand-held douche 100 is illustrated in FIG. 3 whereby an alternate diverter assembly 104a is shown. The diverter assembly 104a comprises a conventional two-branch plumbing connector 160a having an inlet 162a that is adapted for piercing a conventional water supply line 168, such as an existing toilet water supply line, and an outlet branch 166a. A shut-off valve 158a is also provided to permit the user to block the water being syphoned from the water supply line 168 from entering into the hand-held douche apparatus 100. The outlet branch 166a is adapted for receiving one end of flexible tubing 170. As shown in FIGS. 1 and 2, the other end of the flexible tubing 170 is adapted for mating with the inlet port 120 of the cap 118 by means of a conventional coupling or by means of a press-fit, glueing, or other suitable means.

Figure 4:
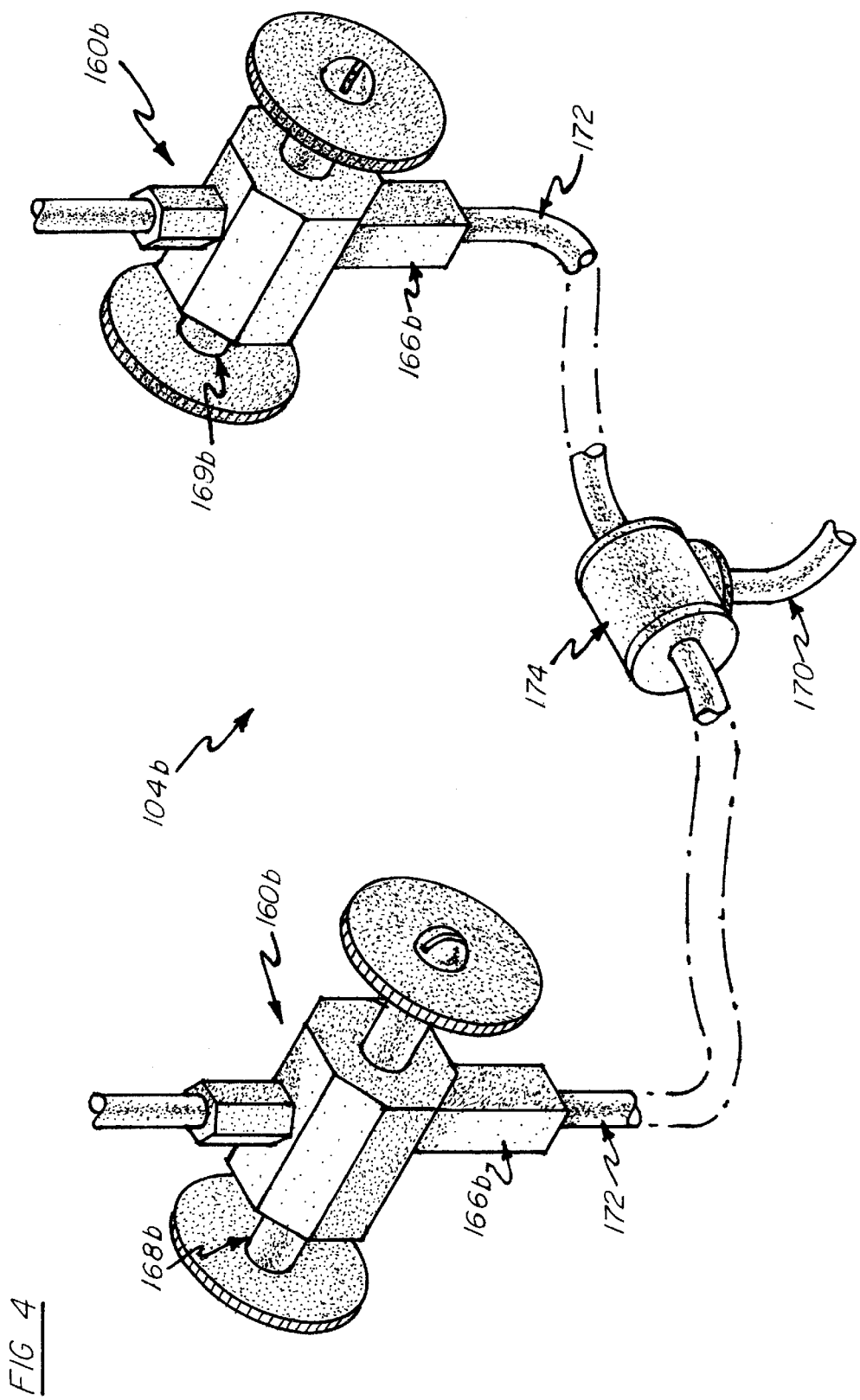
FIG. 4 is a perspective view of another preferred embodiment of the present invention showing another alternate diverter assembly comprising a pair of connectors, one for attaching to a pressurized hot water source and one for attaching to a pressurized cold water source.

As shown in FIG. 4, another preferred embodiment of the hand-held douche apparatus 100 (FIG. 1) is shown whereby the diverter assembly 104b includes a pair of plumbing connectors 160b, each being of the type previously shown (three-branch plumbing connector 160 shown in FIG. 1 or the two-branch pluming connector 160a shown in FIG. 3) one being connected to a cold pressurized water supply line 168b and one being connected to a hot pressurized water supply line 169b. As shown, the outlet branches 166b of the plumbing connectors 160b are adapted for receiving one end of flexible tubing 172. The second end of each flexible tubing 172 is adapted for receiving the stem, (not shown) of a conventional Y-connector 174 which combines the hot and cold water streams into a single water stream which passes through flexible tubing 170 to be received by the mixing assembly 102 (FIG. 1). It should now also be apparent to those skilled in the art that the diverter assembly 104 having plumbing connectors 160b for connecting to hot and cold water sources will permit the user to adjust the temperature of the water stream being dispensed through the spray assembly 106 (FIG. 1).

Figure 5:
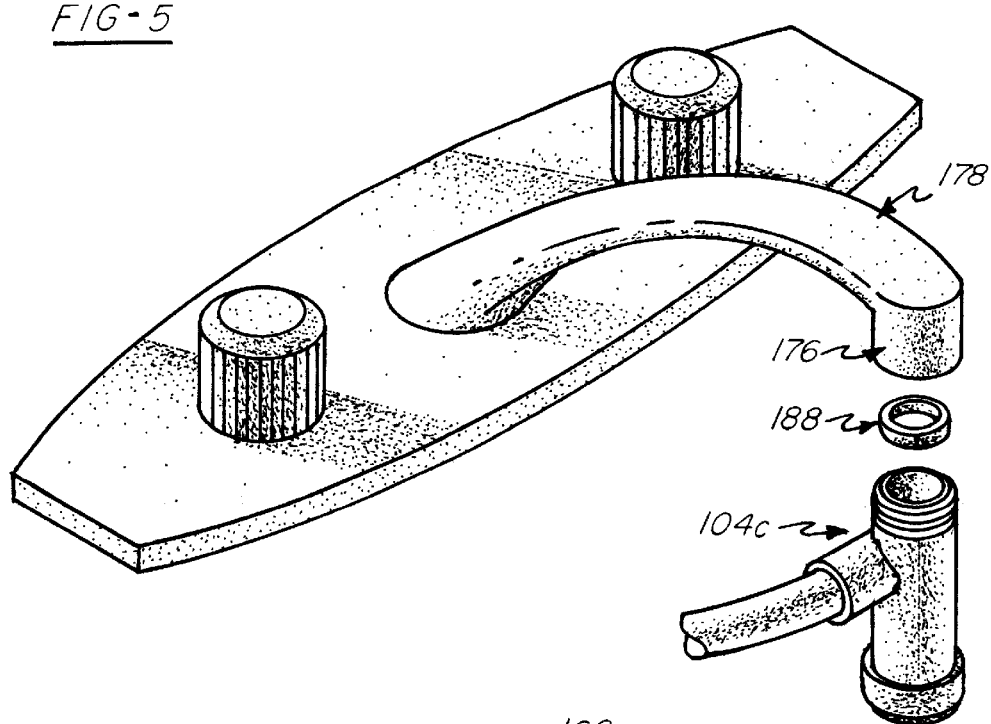
FIG. 5 is a perspective view of another preferred embodiment of the present invention showing an alternate diverter assembly for attaching to a conventional faucet.
Figure 6:
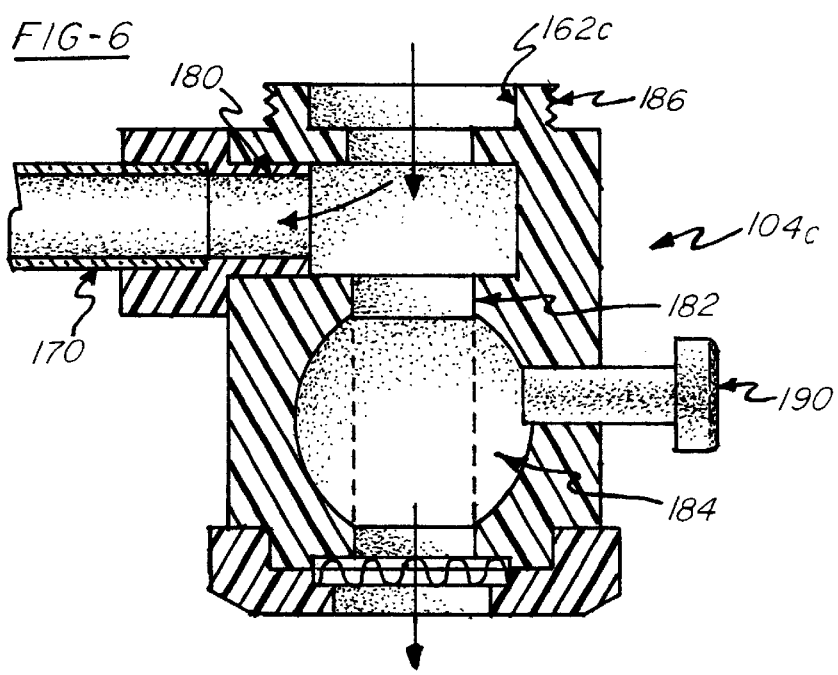
FIG. 6 is a sectional view of the diverter assembly of FIG. 5.

Another preferred embodiment of the hand-held douche 100 is illustrated in FIGS. 5 and 6 whereby another alternate diverter assembly 104c is shown. The diverter assembly 104c comprises an inlet 162c which is adapted for connecting to the outlet 176 of a faucet 178, having a hot and a cold water source such as the faucet typically used for a bathroom sink, and includes a first channel 180 for receiving one end of flexible tubing 170 and a second passage 182 having a conventional on/off valve 184 for allowing or preventing water to flow out through the diverter assembly 104c and into the sink (not shown). The inlet 162c is provided with external threads 186 which correspond and mate with the internal threads (not shown) of the outlet 176 of the faucet 178. It should now be apparent to those skilled in the art that an adapter 188 may be used having one end for connecting to the inlet 162c of the diverter assembly 104c and a second end having external threads which correspond to the particular internal threads of the outlet 176 of the faucet 178. It should now also be apparent to those skilled in the art that by attaching the hand-held douche apparatus 100 to the outlet 176 of a faucet 178 having both hot and cold water sources will permit the user to adjust the temperature of the water stream. It should also now be apparent to those skilled in the art that the diverter assembly 104c having an on/off valve 184 operated by handle 190 permits water to flow through second passage 182 when using the faucet 178 thereby allowing the diverter assembly 104c to remain attached to the faucet 178. When in use, water entering into the diverter 104c through inlet 162c is directed through first channel 180 into flexible tubing 170 for delivery to the mixing assembly 102.

Referring to FIG. 1, the spray assembly 106 includes a first flexible spray hose 192, a second flexible spray hose 194, a handle 144 there between, and a nozzle 198. The spray hoses 192 and 194 can be conventionally connected to the handle 196 and the nozzle 198 such as by connectors, friction fittings, glue or other conventional means. In a preferred embodiment of the invention, as shown, the spray hoses 192 and 194 are conventionally connected to the handle 144 and the nozzle 198 by any suitable means, such as by use of connectors 200 to permit the user to interchange various lengths of spray hoses and nozzles. Further, while one particular design of a nozzle is shown, it should now be apparent to those skilled in the art that various designs of nozzles may be used in the present invention as desired by the user. The handle 144 includes a conventional spring loaded activation valve 142 which cooperate with the handle 144 to allow the user to control the amount of fluid F to be dispensed by the hand-held douche apparatus 100 through the nozzle 198. In operation, the water stream activation valve 142 is in a closed configuration and can be opened by squeezing the actuating lever 202, thereby permitting fluid to flow through the second spray hose 194 and to the nozzle 198. The amount of fluid flow F being discharged through the nozzle 198 can be increased or decreased by increasing or decreasing the squeezing pressure being applied to the actuating lever 202. The activation valve 142 will return to its closed position when the actuating lever 202 is released.

To understand how the elements of this invention described are interrelated, the operation of the hand held douche apparatus 100 will now be described. During operation, water is fed under pressure from the suitable pressurized water supply into the diverter assembly 104 to the inlet port 120 of the mixing assembly through flexible tubing 170. Water will then pass through the first flow passage 124 and the the constricted area 126 and out through outlet port 122. The rapid flow of the water stream passing from the larger diameter inlet port 120 into the smaller diameter constricted area 126, past the opening of the second flow passage 128, and then through the larger diameter outlet port 122 produces a venturi effect such that the pressure in the constricted area 126 is reduced thereby creating a pressure differential that to causes the fluid additive 115 contained in the fluid reservoir 114 to flow upward through the suction tube 138, through the second flow passage 128 and into the constricted area 126 to mix with the water stream. The flow of additive 115 flowing upwardly into the suction tube 138 causes air to be drawn through vent 140 and prevents pressure build-up in the fluid reservoir 114. The amount of additive 115 being induced into the water stream can be easily controlled by rotating the external handle 156 causing the rotary member 154 to rotate thereby increasing or decreasing the amount of restriction to the flow of additive 115 passing through the second flow passage 128. It should now be apparent to those skilled in the art that by rotating the external handle 156 from a first direction, such that the rotary member 154 substantially blocks any additive 115 from passing through the second flow passage 128, to a second position such that the flow of additive 115 is substantially unrestricted, provides the hand-held douche apparatus 100 with the ability to direct a stream of water substantially free of additive to a stream having a substantially high level of additive, or any level there between. The fluid stream then leaves through the outlet port 122 and travels through the first spray hose 192, to handle 144, through second flexible spray hose 194, and into the nozzle 198 where it is discharged. The user by squeezing the actuating lever 202 permits a desired amount of fluid to flow through the second spray hose 194 and to the nozzle 198 where it is discharged. The amount of fluid flow can be increased or decreased by increasing or decreasing the squeezing pressure being applied to the actuating lever 202.

When the user can then cease operations by releasing the actuating lever 202 causing the spring loaded valve to return to its closed position thereby stopping the flow of fluid being discharged from the nozzle 198.

From the foregoing, it should now be apparent to those skilled in the art that new and novel design of the hand-held douche apparatus of the present invention permits the container to be released from the cap for refilling without requiring the apparatus to be disconnected or the water supply to be shut off at the connector. It should also now be apparent to those skilled in the art that by venting the fluid reservoir during operation prevents pressure build up in the reservoir thereby eliminating water spirts and allowing the water stream shut off valve to be located downstream of the storage container. Thus, having the advantages of being relatively easy for the user to control the fluid stream.

There has thus been provided a new and novel hand-held douche apparatus which can be used for personal hygiene; that includes means for mixing an additive, such as a cleansing or medication solution, into the water stream; that permits the user to easily control the amount of additive being induced into the water stream; that permits a water stream having a constant and consistent concentration of additive; and provides means for controlling the pressure of the water stream. The hand-held douche apparatus of the present invention is also relatively inexpensive to manufacture and maintain, is relatively durable, lightweight and simple in construction, easy to operate, and easy to install to conventional plumbing systems.

Although this invention has been shown and described with respect to detailed embodiments thereof, it will be understood by those skilled in the art that various changes in form and detail thereof may be made without departing from the spirit and scope of the claimed invention.

What is claimed is:

1. A hand-held douche apparatus comprising:
   a diverter assembly for receiving a pressurized fluid stream from a fluid source;
   a mixing assembly; and
   a spray assembly;
       wherein said mixing assembly comprising a container having a reservoir for storing a fluid additive and a cap for attaching the container and having a first fluid passage with an inlet port for receiving the pressurized fluid stream from said diverter assembly, an outlet port for directing the pressurized fluid stream to said spray assembly;
       wherein said mixing assembly further comprising means for inducing a fluid additive into the pressurized fluid stream; and
       wherein said mixing assembly further comprising means for preventing the pressurized fluid stream from entering into said reservoir and means for preventing pressure build-up within said reservoir.

2. The hand held douche assembly of claim 1 further comprising means for regulating the amount of additive being induced into the pressurized fluid stream.

3. The hand held douche assembly of claim 1 further comprising means for regulating the temperature of the pressurized fluid stream.

4. The hand-held douche assembly of claim 1 further comprising means for regulating the amount of fluid being dispensed.

5. The hand-held douche assembly of claim 1 wherein said diverter assembly comprises means for connecting to a faucet.

6. The hand-held douche assembly of claim 1 wherein said diverter assembly comprises means for connecting to a hot pressurized water source and a cold pressurized water source.

7. The hand-held douche assembly of claim 1 wherein said spray assembly comprises a nozzle and means for increasing and decreasing the amount of flow being dispensed by through said nozzle.

8. The hand-held douche assembly comprising:
   a diverter assembly for receiving a pressurized fluid stream from a fluid source;
   a mixing assembly; and
   a spray assembly;
       wherein said mixing assembly comprises a container having a reservoir for storing a fluid additive and a cap for attaching the container and having an inlet port for receiving the pressurized fluid stream from said diverter assembly, an outlet port for directing the pressurized fluid stream to said spray assembly, said inlet port and said outlet port interconnected together by a first fluid passage having constricted area;

wherein said mixing assembly further comprising a second fluid passage for providing flow communication with said first fluid passage and said reservoir for inducing the fluid additive into the pressurized fluid stream, and a vent means for venting said fluid reservoir to the outside atmosphere; and wherein said second fluid passage comprises means for preventing the pressurized fluid stream from entering into said reservoir and means for adjusting the amount of additive being induced into the pressurized fluid stream.

9. The hand-held douche apparatus of claim 8 wherein said spray apparatus comprises a handle for controlling the amount of fluid being dispensed by the hand-held douche apparatus.

10. The hand-held douche assembly of claim 8 wherein said diverter assembly comprises means for connecting to a hot pressurized water source and a cold pressurized water source.

11. The hand-held douche assembly of claim 8 wherein said diverter assembly comprises means for connecting to a faucet.

12. The hand-held douche assembly of claim 8 wherein said spray apparatus comprises a handle for controlling the amount of fluid being dispensed by the hand-held douche apparatus and wherein said handle is downstream of said mixing assembly.

13. The hand-held douche assembly of claim 8 wherein said container is removably attached to said cap and wherein said mixing assembly comprises means for permitting said container to be removed while maintaining said fluid stream.

14. The hand-held douche assembly of claim 8 wherein said spray assembly comprises a handle, a nozzle for dispensing said pressurized fluid stream, a flexible hose for directing the pressurized fluid stream from said outlet port to said handle, and means for controlling the amount of pressurized fluid being dispensed from said nozzle.

15. The hand-held douche assembly comprising:

a diverter assembly for receiving a pressurized fluid stream from a fluid source;

a mixing assembly; and a spray assembly;

wherein said mixing assembly comprises a container having a reservoir for storing a fluid additive and a cap for attaching the container and having an inlet port for receiving the pressurized fluid stream from said diverter assembly, an outlet port for directing the pressurized fluid stream to said spray assembly, said inlet port and said outlet port interconnected together by a first fluid passage having constricted area;

wherein said mixing assembly further comprising a second fluid passage for providing flow communication with said first fluid passage and said reservoir for inducing the fluid additive into the pressurized fluid stream, and a vent means for venting said fluid reservoir to the outside atmosphere;

wherein said second fluid passage comprises means for preventing the pressurized fluid stream from entering into said reservoir and means for adjusting the amount of additive being induced into the pressurized fluid stream; and wherein said spray assembly comprises a handle, a nozzle for dispensing said pressurized fluid stream, a flexible hose for directing the pressurized fluid stream from said outlet port to said handle, and means for controlling the amount of pressurized fluid being dispensed from said nozzle.

16. The hand-held douche assembly of claim 15 wherein said diverter assembly comprises means for connecting to a hot pressurized water source and a cold pressurized water source.

17. The hand-held douche assembly of claim 15 wherein said diverter assembly comprises means for connecting to a faucet.

* * * * *